United States Patent
Mills (10) Patent No.: US 8,560,052 B2
(45) Date of Patent: *Oct. 15, 2013

(54) ECHOGENIC MEDICAL DEVICE

(75) Inventor: Stanley L. Mills, Goldsby, OK (US)

(73) Assignee: Core Oncology, Inc., Mercer Island, WA (US)

( * ) Notice: Subject to any disclaimer, the term of this patent is extended or adjusted under 35 U.S.C. 154(b) by 444 days.

This patent is subject to a terminal disclaimer.

(21) Appl. No.: 10/828,539

(22) Filed: Apr. 20, 2004

(65) Prior Publication Data

US 2005/0049490 A1    Mar. 3, 2005

Related U.S. Application Data

(63) Continuation of application No. 09/878,159, filed on Jun. 7, 2001, now Pat. No. 6,732,052.

(51) Int. Cl.
*A61B 6/00* (2006.01)

(52) U.S. Cl.
USPC ........... 600/431; 600/407; 600/458; 600/433; 606/77; 424/1.11

(58) Field of Classification Search
USPC ................ 600/407, 410, 437, 1–8, 431, 458; 128/653, 654; 427/5; 424/1, 9, 1.11; 606/77

See application file for complete search history.

(56) References Cited

U.S. PATENT DOCUMENTS

| | | |
|---|---|---|
| 3,351,049 A | 11/1967 | Lawrence |
| 3,566,125 A | 2/1971 | Linhart et al. ............. 250/462.1 |
| 4,323,055 A | 4/1982 | Kubiatowicz ................ 424/1.11 |
| 4,349,033 A | 9/1982 | Eden ............................. 600/458 |
| 4,401,124 A | 8/1983 | Guess et al. |
| 4,509,506 A | 4/1985 | Windorski et al. ............... 600/8 |
| 4,655,771 A | 4/1987 | Wallsten |
| 4,702,228 A | 10/1987 | Russell et al. ..................... 600/8 |
| 4,704,774 A | 11/1987 | Fujii et al. .................... 29/25.35 |
| 4,763,642 A | 8/1988 | Horowitz ....................... 128/1.2 |
| 4,763,643 A | 8/1988 | Vrzalik |

(Continued)

FOREIGN PATENT DOCUMENTS

| | | |
|---|---|---|
| EP | 0292630 | 10/1987 |
| WO | WO 95/33512 | 12/1995 |

(Continued)

OTHER PUBLICATIONS

Brown, "Design considerations for piezoelectric polymer ultrasound transducers," *IEEE Transactions on Ultrasonics, Ferroelectrics and Frequency Control*, 47:1377-1396, 2000.

*Primary Examiner* — Unsu Jung
*Assistant Examiner* — Joel Lamprecht
(74) *Attorney, Agent, or Firm* — DLA Piper LLP (US)

(57) ABSTRACT

Echogenic medical devices, methods of fabrication and methods of use are disclosed. The device can be adapted to be inserted into a patient. The echogenic construction can be incorporated into the device at the time of fabrication providing acoustic impedance different from that of the surrounding biological tissue or fluid. The medical device is designed for use with an ultrasound imaging system to provide real-time location of the insertion and guidance at the time the device is implanted in a patient, such as in brachytherapy. Following placement of the device the position can be evaluated over time to insure the device remains in proper alignment and functional. Furthermore, the device is designed to incorporate a spacer element at one or both ends to provide separation between radioactive elements.

42 Claims, 5 Drawing Sheets

(56) References Cited

U.S. PATENT DOCUMENTS

| | | | |
|---|---|---|---|
| 4,805,628 A | 2/1989 | Fry et al. | 128/662.02 |
| 4,869,259 A | 9/1989 | Elkins | 600/458 |
| 4,954,126 A | 9/1990 | Wallsten | |
| 4,977,897 A | 12/1990 | Hurwitz | 600/461 |
| 4,994,013 A | 2/1991 | Suthanthiran et al. | 600/8 |
| 4,995,396 A | 2/1991 | Inaba et al. | 128/654 |
| 5,014,708 A | 5/1991 | Hayashi et al. | 128/653 |
| 5,076,278 A | 12/1991 | Vilkomerson et al. | 128/662.03 |
| 5,081,997 A * | 1/1992 | Bosley et al. | 600/458 |
| 5,163,896 A | 11/1992 | Suthanthiran et al. | 600/8 |
| 5,201,314 A | 4/1993 | Bosley et al. | 600/458 |
| 5,289,831 A | 3/1994 | Bosley | 128/899 |
| 5,327,891 A | 7/1994 | Rammler | |
| 5,342,283 A | 8/1994 | Good | 600/8 |
| 5,460,592 A | 10/1995 | Langton et al. | 600/7 |
| 5,490,521 A | 2/1996 | Davis et al. | 600/458 |
| 5,503,614 A | 4/1996 | Liprie | 600/7 |
| 5,611,870 A | 3/1997 | Horne et al. | 136/253 |
| 5,622,687 A | 4/1997 | Krishnan et al. | |
| 5,713,828 A | 2/1998 | Coniglione | 600/7 |
| 5,759,154 A | 6/1998 | Hoyns | 600/458 |
| 5,766,135 A | 6/1998 | Terwilliger | 600/567 |
| 5,769,795 A | 6/1998 | Terwilliger | 600/567 |
| 5,808,020 A | 9/1998 | Ferrieri et al. | 536/18.5 |
| 5,820,549 A | 10/1998 | Marian, Jr. | 600/437 |
| 5,820,554 A | 10/1998 | Davis et al. | 600/431 |
| 5,821,541 A | 10/1998 | Tumer | 250/370.09 |
| 5,833,593 A | 11/1998 | Liprie | 600/3 |
| 5,857,956 A | 1/1999 | Liprie | 600/7 |
| 5,861,226 A | 1/1999 | Horne et al. | 430/5 |
| 5,921,933 A * | 7/1999 | Sarkis et al. | 600/459 |
| 5,924,973 A | 7/1999 | Weinberger | 600/3 |
| 5,976,067 A | 11/1999 | Tucker et al. | 600/2 |
| 5,989,265 A | 11/1999 | De La Joliniere et al. | 606/116 |
| 5,997,463 A | 12/1999 | Cutrer | 600/8 |
| 6,007,475 A | 12/1999 | Slater et al. | 600/8 |
| 6,010,445 A | 1/2000 | Armini et al. | 600/3 |
| 6,018,676 A * | 1/2000 | Davis et al. | 600/431 |
| 6,030,333 A | 2/2000 | Sioshansi et al. | 600/3 |
| 6,045,495 A | 4/2000 | Weinberger | 600/3 |
| 6,045,775 A | 4/2000 | Ericcson et al. | 424/9.36 |
| 6,059,714 A | 5/2000 | Armini et al. | 600/3 |
| 6,060,036 A | 5/2000 | Armini | 424/1.29 |
| 6,060,040 A | 5/2000 | Tournier et al. | 424/9.364 |
| 6,066,083 A * | 5/2000 | Slater et al. | 600/8 |
| 6,074,337 A | 6/2000 | Tucker et al. | 600/2 |
| 6,080,099 A | 6/2000 | Slater et al. | 600/8 |
| 6,086,942 A | 7/2000 | Carden, Jr. et al. | 427/5 |
| 6,099,457 A | 8/2000 | Good | 600/8 |
| 6,099,458 A | 8/2000 | Robertson | 600/8 |
| 6,103,295 A | 8/2000 | Chan et al. | 427/5 |
| 6,106,454 A | 8/2000 | Berg et al. | 600/3 |
| 6,106,473 A | 8/2000 | Violante et al. | 600/458 |
| 6,120,856 A | 9/2000 | Liberti et al. | 427/550 |
| 6,123,920 A | 9/2000 | Gunther et al. | 424/9.322 |
| 6,132,359 A | 10/2000 | Bolenbaugh | 600/8 |
| 6,132,677 A | 10/2000 | Ohriner | 419/67 |
| 6,139,819 A | 10/2000 | Unger et al. | 424/9.52 |
| 6,146,322 A | 11/2000 | Papirov et al. | 600/3 |
| 6,146,615 A | 11/2000 | Davies et al. | 424/9.36 |
| 6,159,142 A | 12/2000 | Alt | 600/3 |
| 6,174,330 B1 | 1/2001 | Stinson | |
| 6,242,742 B1 | 6/2001 | Geay et al. | 250/363.05 |
| 6,347,443 B2 * | 2/2002 | Coniglione | 29/401.1 |
| 6,364,855 B1 * | 4/2002 | Zappala | 604/96.01 |
| 6,398,709 B1 | 6/2002 | Ehr et al. | 600/3 |
| 6,572,525 B1 * | 6/2003 | Yoshizumi | 600/7 |
| 6,585,633 B2 * | 7/2003 | Vitali et al. | 600/7 |
| 6,621,086 B1 * | 9/2003 | Appleby | 250/492.1 |
| 6,648,811 B2 * | 11/2003 | Sierocuk et al. | 600/7 |
| 2002/0022781 A1 * | 2/2002 | McIntire et al. | 600/458 |
| 2002/0183581 A1 * | 12/2002 | Yoe et al. | 600/3 |

FOREIGN PATENT DOCUMENTS

| | | |
|---|---|---|
| WO | WO 96/40352 | 12/1996 |
| WO | WO 97/17104 | 5/1997 |
| WO | WO 97/19706 | 6/1997 |
| WO | WO 97/19724 | 6/1997 |
| WO | WO 98/01186 | 1/1998 |
| WO | WO 99/40970 | 8/1999 |
| WO | WO 00/09211 | 2/2000 |

* cited by examiner

ECHOGENIC MEDICAL DEVICE

CROSS-REFERENCE(S) TO RELATED APPLICATION(S)

This is a continuation of, and claims priority under 35 USC 120 to, patent application Ser. No. 09/878,159, filed Jun. 7, 2001, entitled "Echogenic Medical Device," (now U.S. Pat. No. 6,732,052 issued on Apr. 20, 2004) the entire text of which is expressly incorporated by reference without disclaimer.

BACKGROUND OF THE INVENTION

I. Field of the Invention

The present invention relates generally to the fields of echogenic biomedical devices. More particularly, it provides a brachytherapy device and method of manufacturing echogenic biomedical devices.

II. Description of Related Art

Ultrasonic imaging techniques have become increasingly prevalent in medical diagnosis and therapy over the last decades. The field includes needle biopsy positioning and the identification of medical abnormalities and fetal status in utero. To create echogenicity in an object or device one must provide a difference between the acoustic impedance of the object and the acoustic impedance of the surrounding medium. In the medical field, the surrounding medium is biological tissue or fluids such as blood, cerebral spinal fluid, or urine.

In the field of brachytherapy where radioactive sources are inserted into an organ or diseased tissue the precise placement is critical for calculated dose therapy in the organ or diseased tissue to insure appropriate dosage to the diseased tissue. The location of numerous radioactive sites must be carefully controlled to obtain the necessary radioactive dosing throughout the tumor or disease site. In brachytherapy of the prostate gland, source placement can be determined by ultrasonic imaging of the implant needles located within the gland. The procedure under a sterile field is simple, rapid, and effective provided the gland is implanted with sources in a predetermined array. Following implantation the proper placement must be determined by x-ray or magnetic resonance imaging since current brachytherapy sources are minimally echogenic if at all. If voids are identified a second procedure may be required or additional time may be required to reposition the patient. The field would be greatly improved if the brachytherapy sources were echogenic so as to provide real-time imaging of proper placement of the actual source during the procedure.

For almost two decades a plethora of approaches have been developed to enhance the echogenicity of medical devices by modifying the surface of the device. In U.S. Pat. No. 4,401, 124 issued to Guess et al., the reflection coefficient of a biopsy needle is enhanced by means of a diffraction grating composed of groves diagonally machined into the needle tip. Elkins in U.S. Pat. No. 4,869,259 echogenically enhanced the needle by particle blasting with 50-micron particles to produce a uniformly roughened surface. In U.S. Pat. No. 4,977, 897, Hurwitz machined sounding apertures into needles to match the incident beam wavelength this improving sonographic visibility. Bosley et al. (U.S. Pat. Nos. 5,081,997, 5,201,314 and 5,289,831) modified catheters and other devices by incorporating glass spheres or high-density metal particles in the range of 0.5 to 100 microns or partially spherical indentations. Rammler (U.S. Pat. No. 5,327,891) used micro-bubbles containing medium contained in vanes and/or tracks to echogenically enhance catheters. Davis et al. varied the configuration of the stylet inside the biopsy needle creating a series of annular groves about the stylet to enhance echogenicity of biopsy needles (U.S. Pat. Nos. 5,490,521, 5,820,554, and 6,018,676). In U.S. Pat. No. 5,759,154 Hoyns utilized a masking technique to produce depressions comprising alternating rows of squares and diamonds on the surface around the circumference of the device. Terwilliger modified the stylet by creating concave surfaces on the distal tip end in U.S. Pat. No. 5,766,135 and in U.S. Pat. No. 5,769,795 included a hole in the distal tip end to form a concave surface to reflect the ultrasonic beam. Each of U.S. Pat. Nos. 3,351, 049, 6,099,458, 6,074,337, 4,994,013, 6,080,099, 4,702,228, 5,163,896, 6,132,677, 6,007,475, 5,976,067, 6,030,333, 6,059,714, 5,713,828, 6,132,359, 5,342,283, 6,099,457, 6,010,445, 6,059,714, 6,060,036, 6,146,322, and 6,159,142 disclosure devices with smooth surfaces that are not reflective from all angles. These smooth surfaces, like the smooth surface of a non-treated needle, create a surface that must be perfectly perpendicular to the ultrasonic emitter/receiver to result in an echogenic pattern.

Sarkis et al. in U.S. Pat. No. 5,921,933 claims echogenic enhancement by impregnating the echogenic portion with ultrasonically reflective particles. Violante et al. in U.S. Pat. No. 6,106,473 claimed an ultrasonically visible solid device in which the echogenic coating was applied to a solid matrix where the surface coating comprised bubbles of a non-gas material that changed phase to gas when heated.

However, each of these advancements in the filed of echogenic imaging contains limitations. In many, external modification of the surface is needed. This adds an additional and often expensive step to the manufacturing process. In other methods, the device modifications are such that the orientation of the device must be perfectly aligned with the ultrasonic emitter/receiver in order to be visible using echogenic imaging.

Another disadvantage of the current methods is the lack of means to consistently position implants without the use of additional processing. Current technology often requires the use of a several step process for placing radioactive sources into a tissue site including an imaging step after initial placement to determine where the radioactive sources were actually delivered in the tissue.

It would therefore be advantageous to have a device with enhanced echogenic properties without the need for an extra step in the formation of the device, the need for exacting positioning relative to the ultrasonic emitter/receiver during use, or the need for a separate imaging step during placement of radioactive sources.

SUMMARY OF THE INVENTION

This invention relates to echogenic biomedical devices and methods of preparing them. More particularly, to brachytherapy sources where it is imperative to determine the exact placement of the device within the body at the time of treatment and the placement is not easily visualized. One or all of the following techniques can monitor the post implant position: ultrasonic, radiographic, and/or nuclear magnetic resonance imaging. The device can be used to determine the exact location of tissue for surgical extraction using technology available to the radiologist for placement and the surgeon in the operating room for precise location immediately before the operation and conformation immediately after extraction in the operating room.

An embodiment of the present invention is a medical device having improved echogenic properties comprising a parabolic surface incorporated into the device. The parabolic surface defines a gas-filled body chamber. A radioisotopic component such as $^{26}$Al, $^{198}$Au, $^{115}$Cd, $^{137}$Cs, $^{125}$I, $^{192}$Ir, $^{40}$K, $^{32}$P, $^{103}$Pd, $^{86}$Rb, $^{123}$Sn, $^{89}$Sr, $^{90}$Sr, $^{125}$Te $^{90}$Y, $^{91}$Y, $^{169}$Yb or a combination thereof may be inside the body chamber. Preferably, the radioisotopic components is $^{125}$I or $^{103}$Pd.

It is an aspect of the invention that the device comprises at least one spacer element connected to the body chamber. The device may comprise a plurality of spacer elements such as at least one spacer element at the proximal and/or distal end of the device.

It is an aspect of the invention that the device comprises a plurality of parabolic surfaces, each of the parabolic surfaces defining a body chamber. In certain embodiments, the body chamber may be connected to a spacer element and the spacer element connected to at least a second body chamber. The spacer element or the body chamber may further comprise a contrast material such as silver, gold, or tungsten. The contrast material may be adapted for nuclear magnetic imaging or radiographic imaging.

It is an aspect of the invention that the device may comprise a docking guide operatively attached to the spacer element or to the body chamber wherein the docking guide is at the proximal end of the device. The docking guide is configured to accept a radioactive source or a spacer element and may comprise as flexible joint or a non-locking docking port.

The parabolic surface generally has a density of 0.5-1.5 g/ml, or more preferably 0.8-1.2 g/ml, or even more preferably 0.9 and 1.1 g/ml. The parabolic surface may be adapted to provide multiple angles of reflectance for an ultrasonic beam which is directed at the device.

The device may comprise one or more synthetic polymers such as a liquid crystal polymer (LCP), Teflon, carboxylic polymers, polyacetates, polyacrylics, polyacrylamides, polyamides, polyvinylbutyrals, polycarbonates, polyethylenes, polysilanes, polyureas, polyurethanes, polyethers, polyesters, polyoxides, polystyrenes, polysulfides, polysulfones, polysulfonides, polyvinylhalides, pyrrolidones, rubbers, and thermal-setting polymers. Similarly, the device may comprise a material selected from the group consisting of albumin, cellulose, cellulose derivatives, gelatin, and gut or one or more metals such as titanium.

The device may be adapted to monitor the positioning of the radioisotopic component in a patient.

It is an aspect of the invention that the body chamber defines one or more voids, bubbles or channels. It is preferred that a void is between 0.1 mm and 0.9 mm in length or more preferably about 0.5 mm in length. There may be between 1-100 or more preferably between 1-10 voids in a body chamber. It is preferred that the body chamber defines one void. It is preferred that when the body chamber defines one or more bubbles, the bubbles be between 0.001 and 0.1 mm in diameter, or more preferably about 0.01 mm in diameter. When the body chamber defines one or more channels, they may be between 0.001 and 0.1 mm in diameter or more preferably about 0.01 mm in diameter. The channels may spiral at approximately 45° to the long axis.

The device may be adapted for insertion into a mammal such as a human, and may be adapted for use in brachytherapy.

Another embodiment of the present invention comprises a method of manufacturing an ultrasonically visible device. The method comprises (a) obtaining a liquid crystal polymer (LCP) tube comprising a proximal and a distal end; (b) obtaining a LCP spacer element; (c) placing the spacer element in the proximal end of the LCP tube; (d) sealing the proximal end of the LCP tube containing the spacer element; and (e) sealing distal end of LCP tube, forming a body chamber, wherein the inner surface of the body chamber is a parabolic surface. An optional step of: (f) shaping the body chamber by heating the body chamber to form hemispherical repeating units on the body chamber may also be added. It is preferred that the heating is ultrasonic heating. Step (f) may occur before steps (c), (d) or (e).

The spacer may comprise a contrast agent such as silver, gold or tungsten or more than one spacer elements.

Yet another embodiment of the present invention comprises a method of manufacturing an ultrasonically visible device, the method comprising: (a) obtaining a liquid crystal polymer (LCP) tube comprising a proximal and a distal end; (b) sealing proximal end of the LCP tube; (c) placing a radioisotopic component into the LCP tube; and (d) sealing distal end of LCP tube, forming a body chamber containing the radioisotopic component, wherein the surface of the body chamber is a parabolic surface. An additional step: (e) shaping the body chamber by heating the body chamber to form hemispherical repeating units on the body chamber, may also be included. A preferred form of heating the body chamber is ultrasonic heating. Step (e) may occur before steps (b), (c) or (d).

Another embodiment of the present invention comprises a method of monitoring the implant position in a patient comprising: (a) inserting a medical device into the patient wherein the device comprises a parabolic surface defining a body chamber and a radioisotope component incorporated into the device; (b) directing an ultrasonic beam at the implant position; (c) reflecting signal from the ultrasonic beam off of parabolic surface; (d) collecting reflected ultrasonic signal; and (e) determining the location of the device in the patient from the reflected ultrasonic signal. The method may further comprise surgically extracting tissue from the patient.

An aspect of the invention is that the medical device comprises a nuclear magnetic or radiographic contrast agent and/or a brachytherapy source. More than one of the devices may be inserted in the patient, and the device may be used for breast lesion localization. The location of the device may be determined before an operation or after extraction of tissue from the patient.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1-8 are exemplary drawings of devices conceived as part of the current invention. The particular configurations shown in the figures should not limit the device configuration of the invention in any way. The devices in FIGS. 1-8 each incorporate a spacer segment 1, one or more radiographic and/or NMR high-density material 2, an echogenic surface 3 which may be molded into a ribbed surface or straight, a radioisotope component as a source of radioactivity 4, a hollow gas-filled chamber 5, and an incorporated spacer-docking guide 6.

DESCRIPTION OF ILLUSTRATIVE EMBODIMENTS

I. The Present Invention

The present invention overcomes deficiencies in the art by providing a device for brachytherapy with improved echogenic properties II. Ultrasound Detection Ultrasound devices detect the passage or reflection of sound, or sonotransmissions. Areas of high density will readily reflect echoes. These areas of high density, such as bone or kidney stones, appear bright white on an ultrasound compared to the surrounding soft tissues, such as muscle, surrounding the bone. Air, such as in the bowel, also readily reflects echoes. The edge of the bowel, therefore, appears white on an ultrasound. Therefore substances with widely differing densities (air-bone) may both appear bright white. The invention is directed toward medical devices such as brachytherapy sources and breast lesion localization devices that have enhanced ultrasound visibility by virtue of incorporation of the echogenic surfaces into the design of the device. The device is fabricated to incorporate these surfaces at the time of final assembly, precluding the necessity for subsequent processing such as surface treatment. The device may be injection molded in final design form or extruded in a linear form and during final assembly formed to incorporate the echogenic surface, radiographic, NMR, and radioactive components. The device construction incorporates sonic reflectance as an integral component of the design configuration. Furthermore, to improve the proper placement of the device in the organ the design permits incorporation of spacer elements as an integral part of the device and not a separate device.

II. Echogenic Device

An echogenic surface is a surface that produces an acoustic shadow and can be observed by an ultrasound or echocardiogram. Such a surface is useful when it is necessary to observe the location of a probe when, for example, a radioisotopic source is placed at a specific position within an organ or tissue.

By incorporating a parabolic surface defining a gas-filled chamber into the device design with material similar in density to tissue, the device requires no external surface modification. The "parabolic surface" is defined herein as a surface that is of any design that incorporates configurations into the device that provides multiple angles of reflectance such that the ultrasonic signal is reflected back to the transducer incorporated into the ultrasonic probe. The surface does not have to be truly parabolic in that all internal reflections would pass through the focus. An important aspect of the invention is that the surface allows for reflection at angles other than perpendicular to the long axis of the source. This will increase the amount of signal that is reflected back to the transducer and therefore increase the echogenic property of the source. It is preferred that the majority of the reflected ultrasonic signal will diverge radially from the body cavity of the device such that the signal will be detected by the transducer.

The idea source should reflect ultrasound signal and therefore acoustic shadow at any angle from perpendicular to the long axis to perpendicular to the short axis. The implantation of the source in glandular tissue frequently causes the source to shift or tilt from the original implantation angle. This is due to the spongy nature of the gland, swelling of the tissue, the amount of pressure used to insert the source, and the disruption of the architecture of the gland. Therefore, it is difficult to precisely position a source within a patient at a predefined angle. A flat surface will reflect at a very narrow angle perpendicular the flat surface, and therefore it is much harder to "find" the acoustic signal. As the surface becomes rounded the angle of reflectance will increase because the critical reflecting surface still contains a portion of perpendicular surface. Although this portion is small, it will reflect ultrasound signal back to the transducer.

The shape of the outer surface of the body chamber may be substantially cylindrical, may have two or more hemispherical repeat units, or may be any other shape that provides angles of reflectance for the ultrasonic signal. The hemispherical repeat units are shown, for example, in FIG. 1. The hemispherical repeating units may be formed prior to construction or at any point in the manufacture of the device. The body chamber may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 hemispherical repeat units. The hemispherical units may be of a uniform size and shape, or they may have differing sizes along the device.

a. Body Chamber

The body chamber of the echogenic device is formed between any spacer elements and surrounds the radiotherapy source. The body chamber comprises voids, bubbles or channels filled with a gas such as air or nitrogen. A void may comprise the entire inner dimension of the body chamber, or may comprise part of the inner dimension of the body chamber, with additional voids, radioisotopic components or contrast agents comprising the rest of the inner dimension of the body chamber. Multiple body chambers may be separated from each other by, for example, spacers or material used to form the devices such as a polymer, metal, or biological material.

Bubbles are defined herein as vesicles which are generally characterized by the presence of one or more membranes or walls surrounding an internal void that is filled with a gas such as air. The bubbles may be spherical, partially spherical or may be space filled, and the size of the bubbles is restricted by the maximum diameter of the device and the smallest bubble that can be easily manufactured into the device. The bubbles are preferably between 1.0 µm and 100 µm in diameter. It is more preferred that the bubbles are between 2.0 µm and 50 µm in diameter, or about 10 lm. A bubble diameter of "about 10 µm" means that the average diameter is between 5 µm and 15 µm. The bubbles may be incorporated into the polymer material of the echogenic device. The inner area of the body chamber that is not bubbles may comprise a polymer, metal, or biological material such as the material used to form the device, radioisotopic components, contrast agents, or a transducer.

Channels must have a portion or section that will reflect an ultrasound signal back to the transducer from perpendicular to the long axis to perpendicular to the short axis of the device. The channels may span from 100 µm to the entire length of the body chamber. Preferably, channels diameters are between 1.0 µm and 100 µm in diameter with a preferred diameter of between 2.0 µm and 50 µm in diameter, or about 10 µm. A channel diameter of "about 10 µm" means that the average diameter is between 5 µm and 15 µm. The channels may be incorporated into the polymer material of the echogenic device. The channels may spiral within the body chamber. It is preferred that the spiral occurs at an angle of 35°-55°, 40°-50°, or more preferably approximately 45° to the long axis. The term "approximately 45°" is meant to include angles of between 43° and 47°. Multiple channels may lay parallel or substantially parallel to each other within the body chamber, or channels may be randomly oriented within the body chamber.

b. Spacers

Incorporating spacer elements into the overall design of the device eliminates the need for additional devices that are used to separate the radiation into a uniform grid pattern throughout the organ being treated. The spacer elements in the present invention may be used with or without the echogenic elements and may be used with polymers construction or more current construction of titanium.

Existing technology utilizing spacers or non-deflecting members constructed of woven suture material are prone to jamming in the instillation needle where the needle is "preloaded" with sources. Another implantation procedure utilizes a cartridge to hold only sources without spacers. This second implantation procedure requires one skilled in the art to precisely position the instillation needle at the correct position within the gland or other tissue, instill the source, move the instillation needle to a secondary position, instill a second source, and so on. The therapy outcome is strongly dependent on the blind positioning of the needle in relationship to the previously instilled source. The first source may move during the repositioning phase or migrate down the needle track as the needle is moved into the secondary position. The spacer-incorporated design allows the seconded source to be spaced at a consistent position and reduce migration during the implant procedure. The spacer incorporated design of the present invention permits the "preloading" into needles without the need for separate spacers and may be utilized in the cartridge type instillation procedure permitting the universal application of a single design.

The spacer incorporated brachytherapy source provides consistent placement with either procedure while eliminating the need for secondary processing to produce the non-deflecting type device and production of multiple configurations, thus reducing cost to manufacture and inventory of several products. The spacer may be made out of the same material as the walls of the body chamber, or may be made out of a different material. The spacer may also contain a contrast agent such as an NMR or radiographic contrast agent. An example of such as spacer is a bar of a LCP with a silver rod inserted through the length of the rod.

Spacers may be located on either or both ends of a body chamber; they may also separate two body chambers. Any or all of the spacers may contain a contrast agent. The spacers may all be the same length or may have different lengths.

Figure 7:
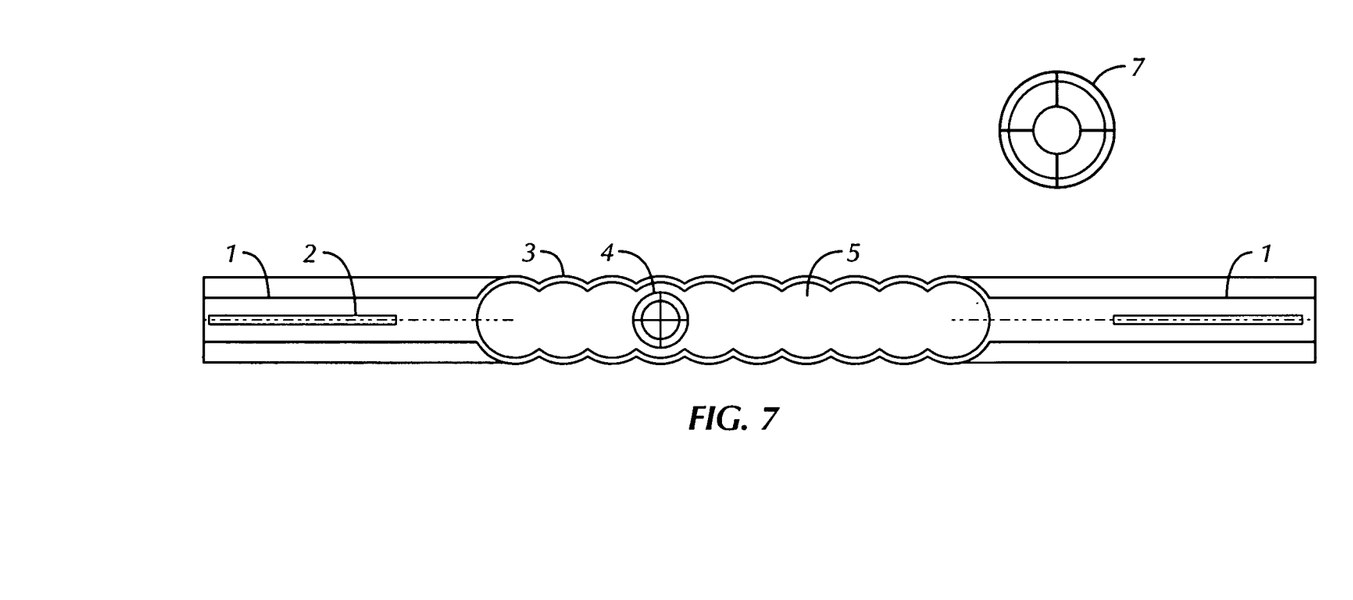
FIG. 7 is an echogenic medical device with a ribbed surface, a radioisotope component, two spacer elements and four struts to increase the rigidity of the spacer sections.

The rigidity of the spacer elements may be increased by incorporating struts in the device. FIG. 7 shows a medical device with a ribbed or hemispherical surface, a spherical radioisotope component, two spacer elements and four struts. There can be 1, 2, 3, 4, 5, 6 or more struts attached to the device. The struts may span the length of the spacer element, may span the length of the device, or may be some intermediate length. Multiple struts may be found on the same device.

c. Spacer Docking Guides

The echogenic device can optionally include a spacer docking guide which can be used to reduce the potential for shingling of the sources during the implantation, to prevent jamming within the implantation needle and to prevent changing the angle of the source in the tissue during placement. The docking guide may be added to the terminal end of a spacer element or body chamber to accept the distal end of the next source thus insuring the sources are implanted in a linear array. The docking guide can be placed on one end or both ends of the echogenic device and can be used to accept the radioisotopic sources into the device. The docking guide can be formed, for example, out of a stainless steel tube with a conical tip.

The docking guide does not necessarily lock onto the echogenic device, and does not lock multiple radioisotope sources together. This reduces the potential for a ridged linear array of implanted radioisotope sources from migration within the organ or other tissue and provides a flexible joint allowing the sources to give at the joint and return to the implanted position.

A flexible joint provided by the docking guide allows the sources to give at the joint and return to the implanted position. The non-locking flexible joint allows multiple sources to move independently of one another preventing motion along the line of sources and preventing the linear array from forcing end sources, either the first or last, from being pushed from the proper placement as one would expect if a long linear array of sources were fixed end to end.

d. Transducers

Transducers are well known in the art, and will convert input electronic signals into an ultrasonic signal. A transducer is incorporated into the ultrasonic probe and will emit an ultrasonic signal towards the echogenic device. The transducer can have a single frequency or multi-frequency output capability. Transducers can perform both transverse and sagittal imaging assays to monitor the position of the seeds in both the longitudinal and transverse planes.

IV. Radioisotopes and Other Imaging Agents

In brachytherapy, radioisotope components are placed inside or in close proximity to diseased or tumor tissue within a patient. The radioactive decay of these isotopes destroys the diseased tissue. However, since the radioisotopes are very small, on the order of 0.5 mCi, the radiation will be localized in the region containing the disease or tumor tissue and will destroy minimal amounts of normal tissue. Other imaging agents can also be incorporated into brachytherapy devices for imaging the device using imaging methods such as NMR (MRI).

a. Radioisotopes

The radioisotope component 4, may be spherical, cylindrical, an oblate or prolate spheroid, or any other shape capable of being inserted into the brachytherapy device. Common radioisotope seed are 0.8 mm by 4.5 mm. but any size seed useful for radiotherapy may be used, such as a seed with dimensions between 0.2 mm and 20 mm. The radioisotope component comprises a radioactive element and optionally a material support such as a resin. The composition of the support is not critical to the current invention. In a preferred embodiment, the radioisotope is small in diameter and is capable of emitting radiation such that a substantially even radial dose function is obtained.

Preferred radioisotopes for use in brachytherapy include low-dose radioactive elements such as $^{125}I$ and $^{103}Pd$ which are left in the patient after treatment. These isotopes have half lives of 60 and 17 days and photon energies of 27-35 keV and 20.1-23 keV respectively. The radiobiological and treatment planning effectiveness of $^{125}I$ and $^{103}Pd$ implants are reviewed by Dicker et al. (2000). The theoretical prediction of effectiveness for the common clinically prescribed total radiation doses indicated that $^{103}Pd$ should be more effective than $^{125}I$ because it had less dependence on tumor cell doubling times. The greatest benefit of $^{103}Pd$ was shown to be with tumors with a short tumor cell doubling times.

For temporary seeds, radioactive elements with a longer half-life can be used. The preferred temporary seeds are usually $^{137}Cs$ and $^{192}Ir$.

Other radioisotopes that can be used for either permanent or temporary seeds include: $^{227}Ac$, $^{241}Am$, $^{243}Am$, $^{249}Cf$, $^{250}Cf$, $^{252}Cf$, $^{242}Cm$, $^{243}Cm$, $^{244}CM$, $^{245}CM$, $^{246}Cm$, $^{237}Np$, $^{231}Pa$, $^{210}Po$, $^{238}Pu$, $^{39}Pu$, $^{40}Pu$, $^{41}Pu$, $^{242}Pu$, $^{23}Ra$, $^{226}Ra$, $^{228}Ra$, $^{227}Th$, $^{228}Th$, $^{230}Th$, $^{230}U$, $^{232}U$, $^{233}U$, $^{234}U$, $^{228}Ac$, $^{110}Ag\ m$, $^{211}At$, $^{140}Ba$, $^{207}Bi$, $^{210}Bi$, $^{49}Bk$, $^{5}Ca$, $^{115}Cd\ m$, $^{144}Ce$, $^{36}Cl$, $^{56}Co$, $^{60}Co$, $^{134}Cs$, $^{137}Cs$, $^{152}Eu$, $^{154}Eu$, $68Ge$, $^{181}Hf$, $^{124}I$, $^{125}I$, $^{126}I$, $^{131}I$, $^{133}I$, $^{114}In\ m$, $^{192}Ir$, $^{54}Mn$, $^{22}Na$, $^{230}Pa$, $^{212}Pb$, $^{224}Ra$, $^{106}Ru$, $^{124}Sb$, $^{125}Sb$, $^{46}Sc$, $^{89}Sr$, $^{90}Sr$, $^{182}Ta$, $^{160}Tb$, $^{127}Te\ m$, $^{129}Te$, $^{234}Th$, $^{204}Tl$, $^{170}Tm$, $^{236}U$, $^{91}Y$, $^{95}Zr$, $^{105}Ag$, $^{111}Ag$, $^{41}Ar$, $^{73}As$, $^{74}As$, $^{76}As$, $^{77}As$, $^{196}Au$, $^{198}Au$, $^{199}Au$, $^{131}Ba$, $^{133}Ba$, $^{7}Be$, $^{206}Bi$, $^{212}Bi$, $^{75}Br$, $^{76}Br76$, $^{82}Br$, $^{14}C$, $^{47}Ca$, $^{109}Cd$, $^{115}Cd$, $^{141}Ce$, $^{143}Ce$ $^{138}C138$ $^{57}Co$, $^{58}Co$, $^{51}Cr$, $^{129}Cs$, $^{143}Cs$, $^{136}Cs$, $^{64}Cs$, $^{67}Cu$, $^{165}Dy$, $^{166}Dy$, $^{161}Er$, $^{169}Er$, $^{171}Er$, $^{152}Eu\ m$, $^{155}Eu$, $^{18}F$, $^{52}Fe$, $^{55}Fe$, $^{59}Fe$, $^{67}Ga$, $^{68}Ga$, $^{72}Ga$, $^{153}Gd$, $^{159}Gd$, $^{175}Hf$, $^{195}Hg\ m$, $^{197}Hg$, $^{197}Hg\ m$, $^{203}Hg$, $^{166}Ho$, $^{123}I$, $^{130}I$, $^{132}I$, $^{134}I$, $^{135}I$, $^{111}In$, $^{115}In$, $^{115}In\ m$, $^{190}Ir$, $^{194}Ir$, $^{42}K$, $^{43}K$, $^{85}Kr\ m$, $^{87}Kr$, $^{140}La$, $^{177}Lu$, $^{28}Mg$, $^{52}Mn$, $^{56}Mn$, $^{99}Mo$, $^{24}Na$, $^{93}Nb\ m$, $^{95}Nb$, $^{147}Nd$, $^{149}Nd$, $^{63}Ni$, $^{63}Ni$, $^{239}Np$, $^{185}Os$, $^{191}Os$, $^{193}Os$, $^{32}P$, $^{233}Pa$, $^{203}Pb$, $^{103}Pd$, $^{109}Pd$, $^{147}Pm$, $^{149}Pm$, $^{142}Pr$, $^{143}Pr$, $^{191}Pt$, $^{197}Pt$, $^{81}Rb$, $^{86}Rb$, $^{183}Re$, $^{186}Re$, $^{188}Re$, $^{105}Rh$, $^{220}Rn$, $^{222}Rn$, $^{103}Ru$, $^{105}Ru$, $^{97}Ru$, $^{35}S$, $^{122}Sb$, $^{47}Sc$, $^{48}Sc$, $^{75}Se$, $^{31}Si$, $^{115}Sm$, $^{153}Sm$, $^{113}Sn$, $^{121}Sn$, $^{125}Sn$, $^{123}Sn$, $^{89}Sr$, $^{90}Sr$, $^{85}Sr$, $^{91}Sr$, $^{92}Sr$, $^{96}Rc$, $^{97}Tc$, $^{97}Tc\ m$, $^{99}Tc$, $^{125}Te\ m$, $^{127}Te$, $^{129}Te$, $^{131}Te\ m$, $^{132}Te$, $^{231}Th$, $^{200}Tl$, $^{201}Tl$, $^{202}Tl$, $^{171}Tm$, $^{239}U$, $^{48}V$, $^{181}W$, $^{185}W$, $^{187}W$, $^{135}Xe$, $^{87}Y$, $^{90}Y$, $^{91}Y$, $^{175}Yb$, $^{169}Tb$ $^{62}Zn$, $^{65}Zn$, $^{69}Zn\ m$, $^{97}Zr$, $^{97}Ar$, $^{11}C$, $^{58}Co\ m$, $^{134}Cs\ m$, $^{135}Cs$, $^{62}Cu$, $^{68}Ga$, $^{71}Ge$, $^{3}H$, $^{129}I$, $^{113}In\ m$, $^{81}Kr\ m$, $^{85}Kr$, $^{13}N$, $^{97}Nb$, $^{59}Ni$, $^{15}O$, $^{191}Os\ m$, $^{193}Pt\ m$, $^{197}Pt\ m$, $^{87}Rb$, $^{187}Re$, $^{103}Rh\ m$, $^{73}Se$, $^{147}Sm$, $^{85}Sr\ m$, $^{87}Sr\ m$, $^{96}Tc\ m$, $^{99}Tc\ m$, Th nat, $^{232}Th$, U nat, $^{235}U$, $^{238}U$, $^{232}Xe\ m$, $^{133}Xe$, $^{91}Y\ m$, $^{69}Zn$ and $^{93}Zr$. Of these isotopes, the isotopes with the preferred half-life and photon energy include $^{26}Al$, $^{198}Au$, $^{115}Cd$, $^{137}Cs$, $^{125}I$, $^{192}Ir$, $^{40}K$, $^{32}P$, $^{103}Pd$, $^{86}Rb$, $^{123}Sn$, $^{89}Sr$, $^{90}Sr$, $^{90}Y$, $^{91}Y$ and $^{169}Yb$.

b. Radiographic Agents

The device may optionally contain a radiographic agent. A radiopaque contrast agent will have radiographic contrast relative to the body and will provide visualization which can be used, for example, as an aid in post treatment evaluation of proper therapeutic array of multiple seeds. Fluoroscopic angiography or X-ray radiation may be used to visualize the contrast agent and deployment and placement of the device in the body.

The contrast agent must have a radiographic density higher than surrounding host tissue and have sufficient thickness to affect the transmission of x-rays to produce contrast in the image. High-density materials such as silver, gold, tungsten, platinum, tantalum, iridium, barium sulfide, bismuth oxide or a blend of two or more high density materials are preferred. Other metals such as stainless steel, superalloys, nitinol, and titanium having lower radiographic densities may also be used. U.S. Pat. Nos. 4,655,771, 4,954,126, 5,061,275 and 6,174,330, herein incorporated by reference describe other contrast agents that may incorporated in to the medical device of the current invention.

c. NMR Contrast Material

Medical diagnostic imaging is an important non-invasive tool for the evaluation of diseased and tumor tissue and seed placement. Presently, nuclear magnetic resonance imaging (MRI or NMR) and computerized tomography (CT) are two of the most widely used imaging modalities. Although both MRI and CT can be performed without the administration of contrast agents, the ability of many contrast agents to enhance the visualization of internal tissues, organs and inserted devices has resulted in their widespread use. Contrast agents can be incorporated in the device for use in MRI imaging.

Proton MRI is based on the principle that the concentration and relaxation characteristics of protons in tissues and organs can influence the intensity of a magnetic resonance image. Contrast agents which are useful for proton MRI effect a change in the relaxation characteristics of protons which can result in image enhancement and improved soft-tissue differentiation.

Contrast agents, such as $F^{3+}$ and any of relevant the isotopes listed herein above may be used as an MRI contrast agent. Other contrast agents useful in this invention for MRI are described in, for example, U.S. Pat. Nos. 6,045,775 and 5,622,687, herein incorporated by reference. Other classes of MRI contrast agents include paramagnetic metal chelates and nitroxyl spin labeled compounds.

V. Echogenic Medical Device Materials

It is preferred that the device be manufactured with the echogenic properties incorporated into the device. This reduces the cost when compared to other "echogenically enhanced" devices where the surface of the device is modified after manufacturing the device. The echogenic device of the current invention may be manufactured with the echogenic properties incorporated in the device.

a. Device Materials

Device materials should have a density similar to that of tissue. A material with a density similar to that of tissue is a one that has a density of 80%-120%, 90%-110%, 95%-105% or 99%-101% of the tissue density. The object of the device material is to have as large as possible density difference between the device material and the air inside and a density as close as possible to tissue as to reduce the reflectance from the outer surface of the device. Any density difference will reflect and scatter the ultrasound. The reflection should come from the parabolic surface. Soft tissues, which are comprised primarily water, will have densities similar to that of water. Liver, heart, muscle, bowel and other tissue will all have similar tissue density. Other tissues, such as bone or kidney stones will have a much greater density than that of the soft tissues.

A preferred substrate material is extruded liquid crystal polymer (LCP) tubing. Other substrate materials include synthetic polymers such as Teflon, carboxylic polymers, polyacetates, polyacrylics, polyacrylamides, polyamides, polyvinylbutyrals, polycarbonates, polyethylenes, polysilanes, polyureas, polyurethanes, polyethers, polyesters, polyoxides, polystyrenes, polysulfides, polysulfones, polysulfonides, polyvinylhalides, pyrrolidones, rubbers, and thermal-setting polymers and natural products such as albumin, cellulose, cellulose derivatives, gelatin, and gut.

The substrate material may be adsorbable by the body, although it is preferred that the device maintain integrity for 1-60 or 1-14 days. Adsorbable materials include, but are not limited to polyester amides of lactic and glycolic acids.

The important characteristics needed when choosing a substrate material for the echogenic device include workability (the material must be able to be, shaped and hermetically sealed), biocompatability and a density similar to tissue.

The material may be extruded, molded, shaped, remanufactured, or manipulated to form the medical device described herein.

The medical device may optionally include a layer of a biocompatible encapsulating material deposited over the parabolic surface of the device.

Materials for the spacer elements may be the same or different than the material forming the body chamber of the device. In one embodiment, spacer elements are made out of an LCP rod while the material forming the body chamber is made from extruded LCP tubing. Alternatively, the spacer element may be formed from a metal such as a titanium rod or stainless steel.

b. Device Dimensions

The wall thickness for the hollow chamber (i.e. LCP tubing thickness) may be about 0.03, 0.04, 0.05, 0.06, 0.07, 0.08, 0.09, 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34 or 0.35 mm thick or thicker. However, the outer diameter (O.D.) of the hollow chamber (i.e. LCP tubing diameter) should be less than 1.0 mm and the I.D. greater than the radioactive carrier O.D and the spacer rod. The O.D. of the spacer rod must be such that it fits inside of the tubing forming the hollow chamber.

As used herein the specification, "a" or "an" may mean one or more. As used herein in the claim(s), when used in conjunction with the word "comprising", the words "a" or "an" may mean one or more than one. As used herein "another" may mean at least a second or more.

X. EXAMPLES

The following example is included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Echogenic Devices

Figure 1:
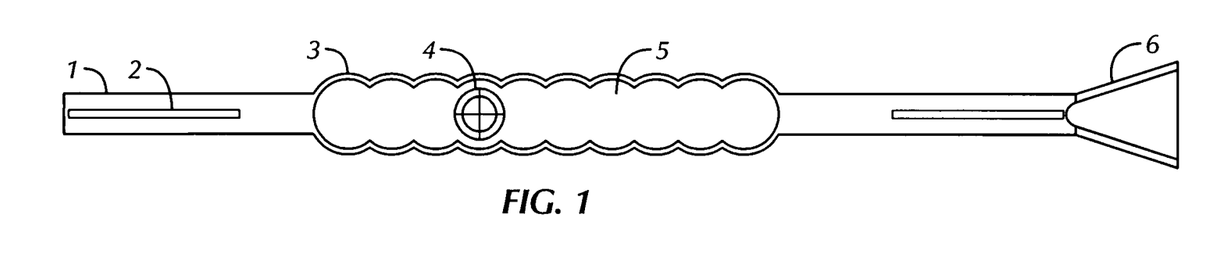
FIG. 1 is an echogenic medical device with a ribbed surface and a spherical radioisotope component in a hollow chamber, two spacer elements, and a spacer docking guide.

FIGS. 1-3, and 5-7 show echogenic devices which comprise one or more ribbed surface (i.e., having hemispherical repeat units) and a hollow gas-filled chamber, one or more spacer elements, and optionally an incorporated spacer-docking guide. Shown in FIG. 1 is one embodiment of the present invention having a single body chamber 5 with a parabolic echogenic surface 3 defining the gas-filled chamber 5. Two spacer elements 1, are found on either side of the body chamber, each of which have a radiographic and/or NMR high-density material 2 in the spacer element. A spacer-docking guide 6 is found at the end of the device.

In FIGS. 1-3, and 7, a hollow air filled chamber 5 enclosed by semi-circular exterior polymeric material 3 hermetically sealing the radioactive source 4 which providing a ultrasonic deflecting surface and high differential gradient to the tissue which the device is implanted. The device is constructed with solid or hollow rods 1 on one or both ends to provide automatic spacing during the implantation process. The device can include a docking guide 6 which is included to prevent jamming within the implantation needle and increase the tissue retention following placement in tissue with a disrupted cellular matrix or glandular composition. To provide radiographic visualization, the current invention includes a high-density material (example: silver) 2 to aid in post treatment evaluation of proper therapeutic array of multiple seeds.

Figure 4:
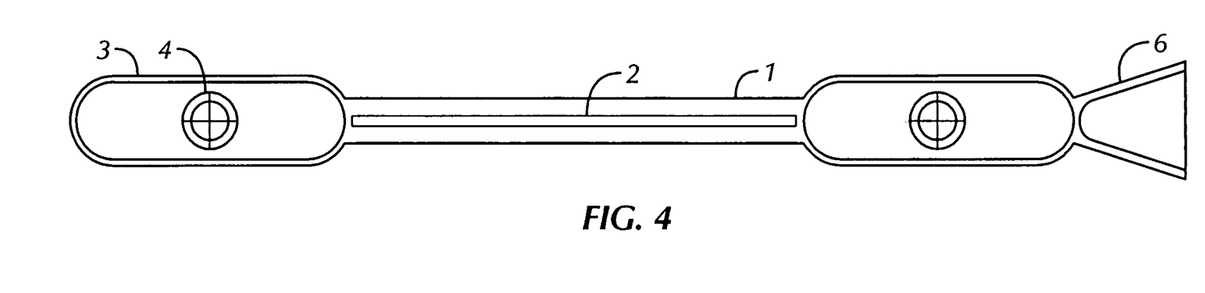
FIG. 4 is an echogenic medical device with two straight surfaces and a radioisotope component in a hollow chamber, a spacer elements, and a spacer docking guide.

FIG. 4 show echogenic devices which comprise one or more parabolic surfaces without modifications to form hemispherical repeat units (ribbing). This embodiment is similar to that shown in FIG. 3 except for the lack of ribbing on the surface. All configurations of the device, such as those described in FIG. 1-2 and 5-8 may incorporate the parabolic surface as shown in FIG. 4.

Figure 2:
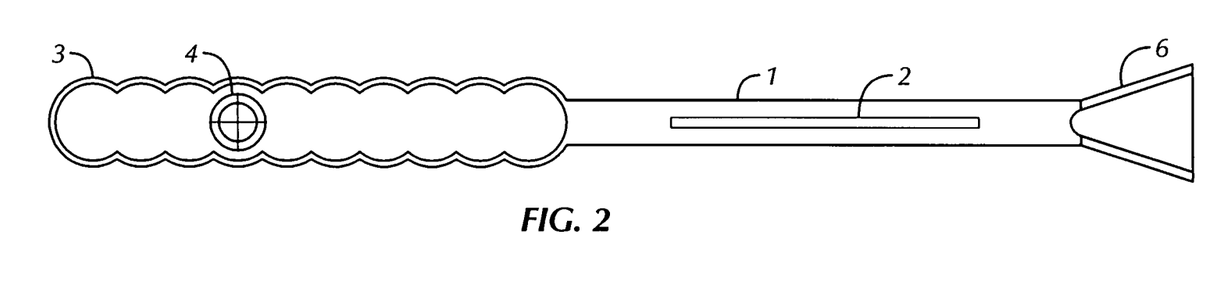
FIG. 2 is an echogenic medical device with a ribbed surface and a spherical radioisotope component in a hollow chamber, a spacer element, and a spacer docking guide.
Figure 3:
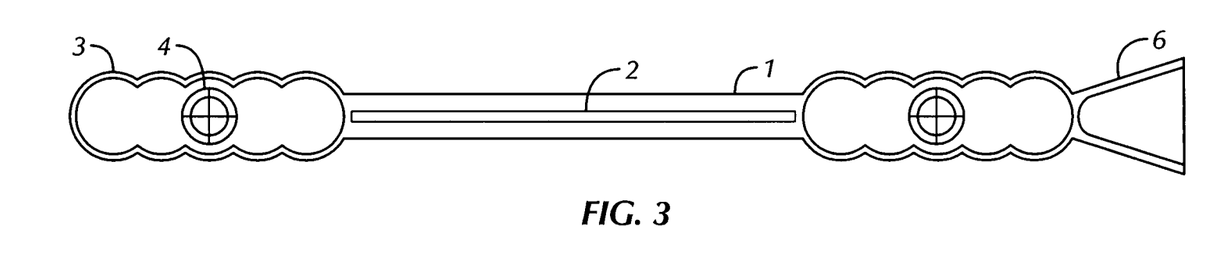
FIG. 3 is an echogenic medical device with two ribbed surfaces and a radioisotope component in a hollow chamber, a spacer elements, and a spacer docking guide.
Figure 5:
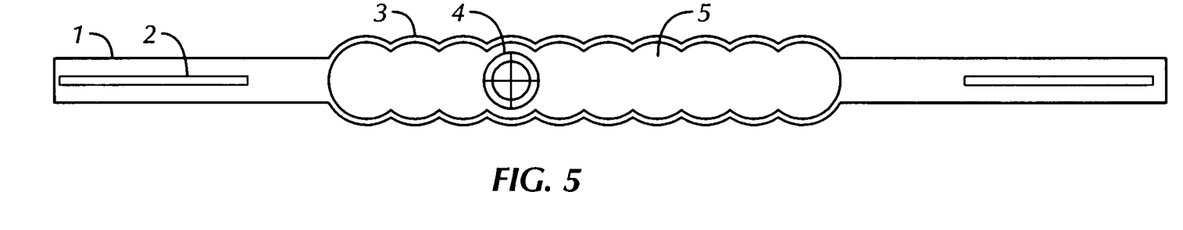
FIG. 5 is an echogenic medical device with a ribbed surface and a radioisotope component chamber and two spacer elements.
Figure 6:
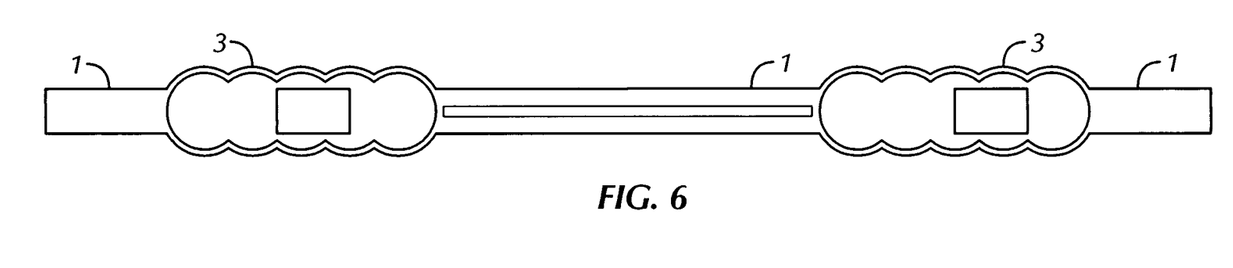
FIG. 6 is an echogenic medical device with two ribbed surfaces and a radioisotope component in a hollow chamber and three spacer elements.

The radioactive material is located centrally and the spacer sections containing the radiographic markers are on each end (i.e. FIGS. 1, 5 and 7). The radiographic contrast material is located centrally to a duel set of radioactive material sources (i.e. FIGS. 3, 4 and 6). Similarly, the radioactive material may be located on one end and the spacer sections containing the radiographic markers on the other (FIG. 2). The device may comprise alternating radioactive material and spacer sections with or without radiographic markers.

A configuration of the current invention may be: spacer-(body chamber-spacer)$_N$-body chamber-spacer, where the spacers on either end are optional and N=0 to 100, or more preferred N=2-10. A docking guide may be attached to either end of the medical device. Alternatively, two seeds may be placed without a spacer between them or two spacers may be placed together.

Example 2

Manufacturing Process

One configuration of the current invention may be manufactured by first cutting to length 10 mm of extruded liquid crystal polymer (LCP) tubing 0.8 mm O.D. with a 0.1 mm wall. Insert into one end a solid rod of LCP 0.4 mm O.D. by 2.75 mm in length containing a central silver wire 0.1 mm O.D. and ultrasonically welding the tubing to the solid rod. A 0.5 mm resin sphere containing one mCi (37 MBq) of Iodine-125 is placed into the open end of the LCP tubing. A second solid rod of LCP 0.4 mm O.D. by 2.75 mm in length containing a central silver wire 0.1 mm O.D. is inserted into the open end of the tubing and the rod ultrasonically welding to the tubing. The final configuration may be used as constructed or further modified by shaping the open hermetically sealed central section into hemispherical repeating units by ultrasonically heating the material and forming FIG. 5.

Another configuration of the current invention may be manufactured by first cutting to length 10 mm of extruded liquid crystal polymer (LCP) tubing 0.8 mm O.D. with a 0.1 mm wall. Insert into one end a solid rod of LCP 0.4 mm O.D. by 2 mm in length containing a central silver wire 0.1 mm O.D. and ultrasonically welding the tubing to the solid rod centered in the LCP tubing. A 0.5 mm resin sphere containing 1 (one) mCi (37 MBq) of Iodine-125 is placed into the open end of the LCP tubing. A second solid rod of LCP 0.4 mm O.D. by 1.0 mm in length without a central silver wire is inserted into this end of the tubing and the rod ultrasonically welding to the tubing. The process is repeated for the opposite end of the source. The two hermetically sealed gaseous three mm chambers may be retained in the linear configuration or shaped into a plurality of hemispherical units as in FIG. 6.

Another configuration FIG. 2 of the current invention may be manufactured by injection molding a LCP capsule 0.8 mm O.D., 0.1 mm wall, and 10 mm in length open on one end. To the open end is added a 0.5 mm resin sphere containing 1 (one) mCi (37 MBq) of Iodine-125. To the open end is inserted a five mm solid rod of LCP 0.4 mm O.D. containing a central silver wire 0.1 mm O.D. leaving one mm of open tubing in which a conically tipped stainless steel rod is inserted to form the docking end and ultrasonically welding the LCP tubing to the solid rod and forming the docking end.

Example 3

Manufacturing the Hemispherical Repeating Units

The echogenic surface of the device may comprise the surface of the extruded LPC tubing, as shown in FIG. 4, or it may be further modified by shaping the open hermetically sealed central section into hemispherical repeating units by ultrasonically heating the material as depicted in FIGS. 1-3 and 5-7. The hemispherical repeating units may be formed into the stock LCP prior to construction or at any point in the process including at the point of welding the first or second LCP rods.

Example 4

Comparison of Radial Dose Function and Radiation Shadow

Figure 8:
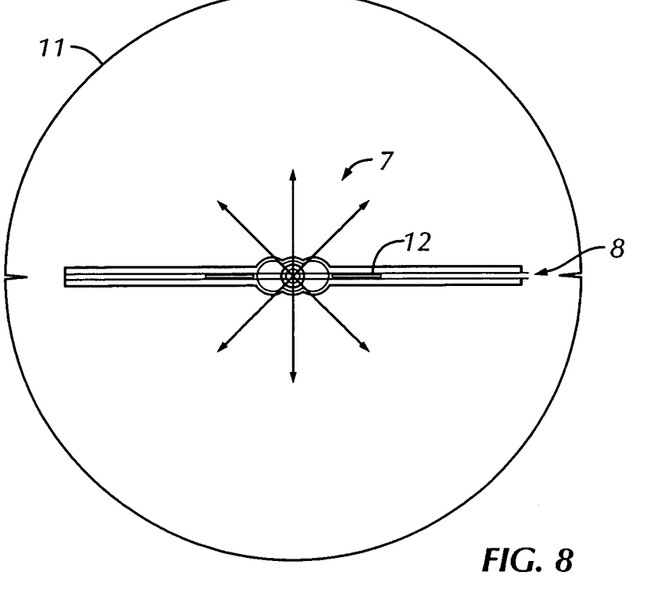
FIG. 8 is an echogenic medical device with an improved radial dose function and radiation shadow.
Figure 9:
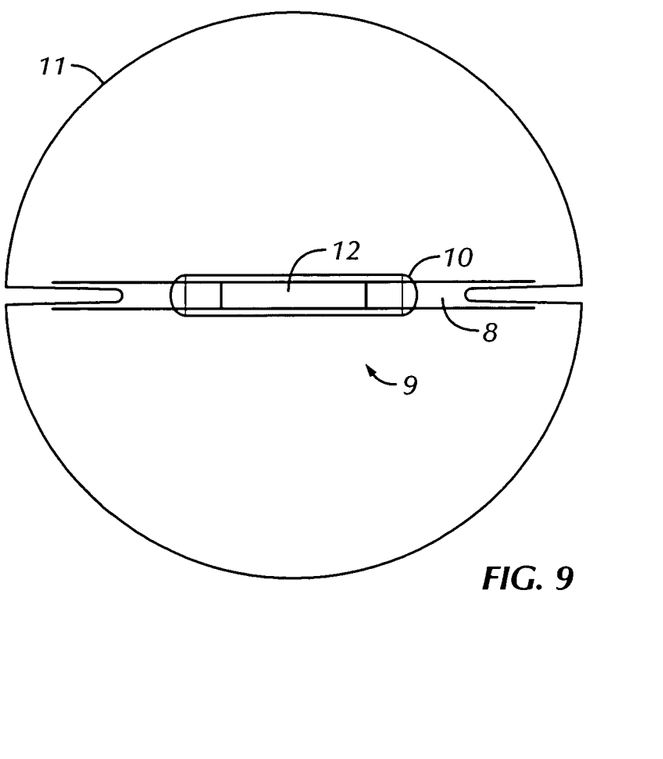
FIG. 9 is a device as described in U.S. Pat. No. 4,323,055, where the radial dose function and radiation shadow of the device is not reflective from all angles.

FIG. 8 and FIG. 9 demonstrate the improved radial dose function 11 and the radiation shadow 8 comparisons between the present invention (FIG. 8) and current technology as described in U.S. Pat. No. 4,323,055 currently distributed by Nycomed Amersham (FIG. 9). The devices described in U.S. Pat. No. 4,323,055 and shown in FIG. 9 comprises a titanium tube hermetically sealed by welding the tube ends 10 closed. Inside the sealed tube is contained a silver wire 12. The radioisotope material 4 is adsorbed onto the exterior of the wire 12. The surface of the radioisotope source 4 perpendicular to the long axis 9 has a higher exposure to the tissue being treated than the area of the radioisotope source 4 perpendicular to the short axis 8. This results in a nonsymmetrical dose field where the different regions of the tumor or diseased tissue obtain varied and uneven radiation exposure. This limitation in isotropy is due in part to the larger surface area of the long axis and the thickness of the welded ends of the titanium tube. Also, the radiographic contrast material is located interior to the radioactivity in the source as shown in FIG. 9 attenuates the emission because the decay emits into the contrast material and not into the tumor or diseased tissue.

The current invention, with the radial dose function depicted in FIG. 8, is designed to create a "point" source of radioactivity. The radiographic contract component 12 in the current invention is preferably small in diameter compared to the diameter of the component containing the radioactive material in the Nycomed Amersham device. This greatly reducing both the extent of the decrease and the area of diminished exposure perpendicular to the short axis. In the present invention, when the radioisotope is loaded on the periphery of the sphere, a crossfire effect is created exposing more area distal to the source.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Dicker A P, Lin C C, Leeper D B, Waterman F M. "Isotope selection for permanent prostate implants? An evaluation of 103Pd versus 125I based on radiobiological effectiveness and dosimetry" Semin Urol Oncol 2000 May;18(2):152-9.

U.S. Pat. No. 3,351,049
U.S. Pat. No. 4,323,055
U.S. Pat. No. 4,401,124
U.S. Pat. No. 4,655,771
U.S. Pat. No. 4,702,228
U.S. Pat. No. 4,763,643
U.S. Pat. No. 4,869,259
U.S. Pat. No. 4,954,126
U.S. Pat. No. 4,977,897
U.S. Pat. No. 4,994,013
U.S. Pat. No. 5,061,275
U.S. Pat. No. 5,081,997
U.S. Pat. No. 5,163,896
U.S. Pat. No. 5,201,314
U.S. Pat. No. 5,289,831
U.S. Pat. No. 5,327,891
U.S. Pat. No. 5,342,283
U.S. Pat. No. 5,490,521
U.S. Pat. No. 5,622,687
U.S. Pat. No. 5,713,828
U.S. Pat. No. 5,759,154
U.S. Pat. No. 5,766,135
U.S. Pat. No. 5,769,795
U.S. Pat. No. 5,820,554
U.S. Pat. No. 5,921,933
U.S. Pat. No. 5,976,067
U.S. Pat. No. 6,007,475
U.S. Pat. No. 6,010,445
U.S. Pat. No. 6,018,676
U.S. Pat. No. 6,030,333
U.S. Pat. No. 6,045,775
U.S. Pat. No. 6,059,714
U.S. Pat. No. 6,059,714
U.S. Pat. No. 6,060,036
U.S. Pat. No. 6,074,337
U.S. Pat. No. 6,080,099
U.S. Pat. No. 6,099,457
U.S. Pat. No. 6,099,458
U.S. Pat. No. 6,106,473
U.S. Pat. No. 6,132,359
U.S. Pat. No. 6,132,677
U.S. Pat. No. 6,146,322
U.S. Pat. No. 6,159,142
U.S. Pat. No. 6,174,330

I claim:

1. An implantable brachytherapy seed device configured to be imaged, the device comprising: a parabolic surface defining a hermetically sealed body chamber filled with a gas; and a radioisotopic component inside the body chamber that is surrounded by the gas wherein the gas has a density difference with the body chamber and the tissue into which the implantable brachytherapy seed device is implantable so that the implantable brachytherapy seed is more easily imagable using acoustic energy, the medical device having a proximal and a distal end and the medical device is capable of being implanted into a live body.

2. The device of claim 1, where the radioisotopic component comprises $^{26}$Al, $^{198}$Au, $^{115}$Cd, $^{137}$Cs, $^{125}$I, $^{192}$Ir, $^{40}$K, $^{32}$P, $^{103}$Pd, $^{86}$Rb, $^{123}$Sn, $^{89}$Sr, $^{90}$Sr, $^{125}$Te, $^{90}$Y, $^{91}$Y, $^{169}$Yb or a combination of these.

3. The device of claim 2, where the radioisotopic component comprises $^{125}$I or $^{103}$Pd.

4. The device of claim 1, where the device comprise at least one spacer element connected to the body chamber.

5. The device of claim 4, further comprising at least one spacer element at the proximal end of the device.

6. The device of claim 4, further comprising at least one spacer element at the said distal end of the device.

7. The device of claim 4, further comprising a plurality of parabolic surfaces, each parabolic surface defining a body chamber.

8. The device of claim 7, where one body chamber is connected to a spacer element that is connected to at least a second body chamber.

9. The device of claim 4, the spacer element further comprising a contrast material.

10. The device of claim 9, where the contrast material is silver, gold, or tungsten.

11. The device of claim 4, further comprising a docking guide that is operatively attached to the spacer element or to the body chamber where the docking guide is at the proximal end of the device.

12. The device of claim 11, wherein the docking guide accepts a radioactive source or a spacer.

13. The device of claim 11, wherein the docking guide fixes the medical device in tissue when the medical device is implanted into a live body.

14. The device of claim 11, where the docking guide comprises a flexible joint.

15. The device of claim 11, where the docking guide comprises a non-locking docking port.

16. The device of claim 1, further comprising a plurality of spacer elements.

17. The device of claim 16, wherein the plurality of spacer elements further comprises at least one spacer element at the proximal end and at least one spacer element at the distal end of the device.

18. The device of claim 1, further comprising a contrast material inside the body chamber.

19. The device of claim 18, where the contrast material further comprises a nuclear magnetic imaging contrast material.

20. The device of claim 18, where the contrast material further comprises a radiographic imaging contrast material.

21. The device of claim 1, where the device has a density of between 0.5 and 1.5 g/ml.

22. The device of claim 1, where the device has a density of between 0.8 and 1.2 g/ml.

23. The device of claim 1, where the device has a density of between 0.9 and 1.1 g/ml.

24. The device of claim 1, where the device comprises one or more synthetic polymers.

25. The device of claim 24, where the polymer is selected from the group consisting of liquid crystal polymer (LCP), Teflon, carboxylic polymers, polyacetates, polyacrylics, polyacrylamides, polyamides, polyvinylbutyrals, polycarbonates, polyethylenes, polysilanes, polyureas, polyurethanes, polyethers, polyesters, polyoxides, polystyrenes, polysulfides, polysulfones, polysulfonides, polyvinylhalides, pyrrolidones, rubbers, and thermal-setting polymers.

26. The device of claim 25, where the polymer is LCP.

27. The device of claim 26, where the LCP is an extruded LCP.

28. The device of claim 1, where the device comprises a material selected from the group consisting of albumin, cellulose, cellulose derivatives, gelatin, and gut.

29. The device of claim 1, where the device comprises one or more metals.

30. The device of claim 29, where the metal is titanium.

31. The device of claim 1, further comprising one or more voids, bubbles or channels.

32. The device of claim 31, where each void is between 0.1 mm and 0.9 mm in length.

33. The device of claim 32, where each void is about 0.5 mm in length.

34. The device of claim 32, comprising 1-10 voids.

35. The device of claim 34, comprising 1 void.

36. The device of claim 31, where each of the bubbles are between 0.001 and 0.1 mm in diameter.

37. The device of claim 36, where each of the bubbles are about 0.01 mm in diameter.

38. The device of claim 31, where each of the channels are between 0.001 and 0.1 mm in diameter.

39. The device of claim 38, where each of the channels are about 0.01 mm in diameter.

40. The device of claim 38, where each of the channels spiral at approximately 45 degree to the long axis.

41. The device of claim 1, wherein the gas is air.

42. The device of claim 1, wherein the gas is nitrogen.

* * * * *